United States Patent [19]

Doyle et al.

[11] 4,022,780
[45] May 10, 1977

[54] PROCESS FOR THE MANUFACTURE OF INDOLE DERIVATIVES

[75] Inventors: Martin Doyle; Stephen Collyer Smith, both of Macclesfield, England

[73] Assignee: Imperial Chemical Industries Limited, London, England

[22] Filed: Apr. 22, 1976

[21] Appl. No.: 679,224

Related U.S. Application Data

[63] Continuation of Ser. No. 441,389, Feb. 11, 1974, abandoned.

[30] Foreign Application Priority Data

Mar. 6, 1973 United Kingdom ............ 10736/73

[52] U.S. Cl. .................. 260/256.4 Q; 260/256.5 R
[51] Int. Cl.$^2$ .................................... C07D 239/72
[58] Field of Search ............. 260/256.4 Q, 256.5 R

[56] References Cited

UNITED STATES PATENTS

| | | | |
|---|---|---|---|
| 3,190,889 | 6/1965 | Shen | 260/256.4N |
| 3,833,587 | 9/1974 | Gabel | 260/256.4 Q |
| 3,884,919 | 5/1975 | Birchall et al. | 260/256.4 Q |

Primary Examiner—Leonard Schenkman
Attorney, Agent, or Firm—Cushman, Darby & Cushman

[57] ABSTRACT

Manufacture of 1-(quinazolin-4-yl)indol-3-ylacetic acids and salts thereof by reacting a phenylhydrazone derivative with a quinazoline derivative, for example a halogenoquinazoline, and then ring-closing the resulting intermediate product. An illustrative product of the process of the invention is 1-(7-chloroquinazolin-4-yl)-5-methoxy-2-methylindol-3-ylacetic acid.

3 Claims, No Drawings

PROCESS FOR THE MANUFACTURE OF INDOLE DERIVATIVES

This is a continuation, of application Ser. No. 441,389 filed Feb. 11, 1974, now abandoned.

This invention relates to a process for the manufacture of indole derivatives and more particularly it relates to a process for the manufacture of new 1-heterocyclic-indol-3-yl carboxylic acids which possess anti-inflammatory, analgesic and antipyretic activity.

According to the invention there is provided a process for the manufacture of compounds of the formula:

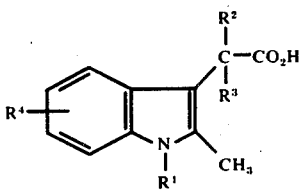

wherein $R^1$ stands for a quinazolin-4-yl radical which may optionally bear a $C_{1-5}$-alkyl, $C_{1-5}$-alkylthio or halogen substituent, and $R^2$ and $R^3$, which may be the same or different, stand for hydrogen or a methyl radical, and $R^4$ stands for hydrogen or a $C_{1-5}$-alkoxy or $C_{1-5}$-alkyl radical, and pharmaceutically-acceptable salts thereof, which comprises reacting a compound of the formula:

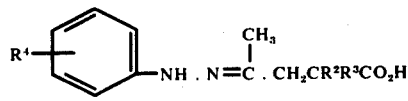

wherein $R^2$, $R^3$ and $R^4$ have the meanings stated above, with a compound of the formula $R^1Y$, wherein $R^1$ has the meaning stated above and Y stands for a leaving group, for example a chlorine, bromine or iodine atom, so as to give a compound of the formula:

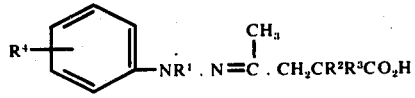

wherein $R^1$, $R^2$, $R^3$ and $R^4$ have the meanings stated above, which is present as its salt, and then ring-closing the said compound of the formula III so as to give the appropriate carboxylic acid of the formula I, which, if desired, is converted into a pharmaceutically-acceptable salt by known means.

The substituent which may optionally be present in the heterocyclic radical $R^1$ may, for example, be selected from methyl, ethyl, propyl, methylthio, fluoro, chloro and bromo substituents. A suitable value for $R^4$ is, for example, hydrogen or a methoxy, ethoxy, propoxy, methyl, ethyl, propyl or butyl radical.

Salts of the compounds of the formula III which are suitable for use in the second stage of the process are acid-addition salts, for example a hydrochloride.

Suitable salts which may be obtained as products of the process of this invention are salts in which the anion is derived from a compound of the formula I and the cation is a pharmaceutically-acceptable cation, for example an alkali metal salt, alkaline earth metal salt, aluminum salt or ammonium salt, or a salt with a pharmaceutically-acceptable organic base, for example triethanolamine.

Compounds which are obtainable according to the process of this invention are, for example, 1-(7-chloroquinazolin-4-yl)-5-methoxy-2-methylindol-3-ylacetic acid, 1-(7-chloroquinazolin-4-yl)-2,5-dimethylindol-3-ylacetic acid, 2-methyl-1-(2-methylquinazolin-4-yl)indol-3-ylacetic acid, 2-methyl-1-(quinazolin-4-yl)indol-3-ylacetic acid, 1-(7-chloroquinazolin-4-yl)-2-methylindol-3-ylacetic acid, 5-methoxy-2-methyl-1-(2-methylquinazolin-4-yl)indol-3-ylacetic acid, and 5-methoxy-2-methyl-1-(2-methylthioquinazolin-4-yl)indol-3-ylacetic acid, and pharmaceutically-acceptable salts thereof.

In the process of this invention the intermediate of the formula III may be isolated and purified prior to the ring-closure stage. Alternatively, this isolation and purification may be omitted, or at the end of said first stage the reaction mixture may be partially purified prior to the ring-closure stage.

The first stage of the process is conveniently carried out in a dry, relatively high boiling, inert organic solvent, for example such a solvent of boiling point 50° to 200° C., for example 1,2-dimethoxyethane, diethyleneglycol dimethyl ether, dioxan, diphenyl ether, tetrahydrofuran or 1,2-dichloroethane, or a mixture of any of these solvents. The first stage is conveniently carried out at 0° to 50° C., and more particularly at 15° to 25° c. A catalytic amount of a saturated solution of hydrogen chloride in a $C_{1-4}$-alkanol, for example isopropanol, may optionally be added to the reaction mixture.

The second or ring-closure stage is conveniently carried out in an organic solvent, for example an aromatic hydrocarbon solvent, for example toluene or xylene, or a di-$C_{1-4}$-alkyl-formamide, for example dimethylformamide, or formic, acetic, propionic or laevulinic acid, or a mixture of any of these solvents. The ring-closure is carried out by heating the reaction mixture at 40° to 160° C., for example reflux temperature, conveniently under acidic conditions. Suitable acidic conditions are provided by the presence in the reaction mixture of a Lewis acid, for example anhydrous zinc chloride or boron trifluoride etherate, or sulphuric, perchloric, laevulinic or formic acid, or polyphosphoric acid or a $C_{1-5}$-alkyl ester thereof, for example the ethyl ester thereof, or a hydrogen halide, for example hydrogen chloride. When the intermediate of the formula III is not isolated prior to the ring-closure stage, the hydrogen halide of the formula HY, wherein Y has the meaning stated above, which is generated in the first stage of the reaction in the case where Y stands for a chlorine, bromine or iodine atom, can provide the said acidic conditions.

The starting materials of the formula II may be obtained by reacting a phenylhydrazine of the formula:

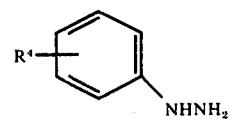

wherein $R^4$ has the meaning stated above, with a compound of the formula:

wherein $R^2$ and $R^3$ have the meanings stated above, at −5° C. to room temperature, optionally in toluene. A catalytic amount of an acid, for example acetic, sulphuric, hydrochloric or perchloric acid, may optionally also be present.

The anti-inflammatory activity of the compounds which are obtained according to the process of this invention has been demonstrated in two well known tests involving adjuvant induced arthritis and carrageenin induced oedema in the rat; their analgesic activity has been demonstrated in the so-called mouse squirm test (using acetic acid) and in another test involving established arthritis in rats; and their antipyretic activity has been demonstrated in a standard antipyretic test in rats. The activity in these tests depends upon the chemical structure of the particular compound being tested, but generally speaking the compounds show activity at a dose in the region 0.5 to 100mg./kg. No toxic effects or undesirable side effects have been observed in the rat or mouse with the compounds at doses at which they show activity in the above-mentioned tests.

When a compound obtained according to the process of this invention is used as an anti-inflammatory, analgesic or antipyretic agent in the treatment of warm-blooded mammals, for example man, for example for the treatment of rheumatoid arthritis, it is recommended that it be administered orally at a total daily dose of 25 to 1000mg. per 70kg. bodyweight, for example as an aqueous or non-aqueous solution or suspension or as a dosage unit form, for example a tablet or capsule comprising 5 to 250mg. of the said compound. Alternatively, the compound may be dosed rectally as a suppository at a total daily dose of 25 to 1000mg. per 70kg. bodyweight, or it may be administered topically as necessary.

The invention is illustrated by the following Examples:

EXAMPLE 1

Laevulinic acid p-methoxyphenylhydrazone (1.2g.) was added to a solution of 4,7-dichloroquinazoline (1g.) in dry 1,2-dimethoxyethane (20ml.). Two drops of a saturated solution of hydrogen chloride in isopropanol were added. The mixture was kept at room temperature for 18 hours, and the 1,2-dimethoxyethane was then decanted, leaving a dark oily solid. Ethyl acetate (50ml.) was added to this, and the mixture was stirred at room temperature for 30 minutes. The mixture was filtered, and the solid residue washed with ethyl acetate (5ml.) and then dried in air at room temperature. There was thus obtained laevulinic acid N'-(7-chloroquinazolin-4-yl)-N'-p-methoxyphenylhydrazone hydrochloride, m.p. 149°–151.5° C.

A mixture of the above hydrazone hydrochloride (0.8g.) and anhydrous zinc chloride (fused prior to the reaction; 0.2g.) in toluene (80ml.) was stirred and heated under reflux for 9 hours. The toluene was evaporated in vacuo and the residue was dissolved in a mixture of ammonium hydroxide (d = 0.86; 5ml.) and water (50ml.). The mixture was filtered, and the filtrate cooled to 0° C. The cooled solution was stirred and glacial acetic acid was added dropwise until the resulting mixture was pH 4. The mixture was filtered, and the solid residue washed with distilled water and dried in air at room temperature. There was thus obtained a hydrate of 1-(7-chloroquinazolin-4-yl)-5-methoxy-2-methylindol-4-ylacetic acid, m.p. 110°–112° C.

The hydrazone used as starting material was obtained as follows:

A solution of laevulinic acid (6.25g.) in toluene (25ml.) was added dropwise over 5 minutes to a stirred suspension of p-methoxyphenylhydrazine (8.5g.) in toluene (100ml.) which was kept at −5° C. under a nitrogen atmosphere. When the addition was completed the reaction mixture was allowed to warm up slowly to room temperature, and it was then stirred at room temperature for 18 hours. The resulting mixture was filtered, and the solid residue was washed with toluene and dried in vacuo at room temperature. There was thus obtained laevulinic acid p-methoxyphenylhydrazone, m.p. 109°–114° C. (decomposition).

EXAMPLE 2

The reactions described in Example 1 were repeated except that the p-methoxyphenylhydrazine was replaced by an equivalent amount of p-tolylhydrazine. There was thus obtained 1-(7-chloroquinazolin-4-yl)-2,5-dimethylindol-3-ylacetic acid, m.p. 102°–105° C.

EXAMPLE 3

The appropriate reactions described in Example 1 were repeated, but using levulinic acid phenylhydrazone and 4-chloro-2-methylquinazoline as starting materials, and there was thus obtained 2-methyl-1-(2-methylquinazolin-4-yl)-indol-3-ylacetic acid as an amorphous hemi-hydrate, m.p. 95°–100° C. (decompositon), [NMR: 2-$CH_3$(indole ring) at 7.7τ; 2-$CH_3$ (quinazoline ring) at 8.1τ]. The intermediate laevulinic acid N'-(2-methylquinazolin-4-yl)-N'-phenylhydrazone hydrochloride had m.p. 95° to 102° C. (decomposition).

EXAMPLE 4

A solution of 4,7-dichloroquinazoline (4.0g.) in 1,2-dichloroethane [50ml.: dried over sodium alumino-silicate (molecular sieve 4A; obtainable from BDH Chemicals Ltd., Poole, Dorset, England)] was added to a solution of laevulinic acid p-methoxyphenylhydrazone (4.5g.) in 1,2-dimethoxyethane (30ml.; dried over sodium alumino-silicate, see above). The mixture was stirred at room temperature for 16 hours and then evaporated in vacuo. The residue was dissolved in formic acid (100ml.) and the solution heated under reflux for 6 hours. Concentration in vacuo gave a red syrup, to which was added water (100ml.) and ethyl acetate (100ml.). The aqueous phase was separated and further extracted with ethyl acetate (2 × 50ml.). The combined organic extracts were back-extracted with 2N-ammonium hydroxide (4 × 100ml.). The combined aqueous extracts were acidified by the addition of concentrated hydrochloric acid to give a pH of 3 to 4, and the oily solid which separated was extracted with ethyl acetate (3 × 50ml.). The combined organic extracts were washed with water (40ml.), dried ($MgSO_4$) and evaporated. The stiff syrup thereby obtained crystallised on the addition of methanol (4ml.) to give 5-methoxy-2-methyl-1-(7-chloroquinazolin-4-yl)indol-3-ylacetic acid, m.p. 202°–204° C.

In a similar manner, starting with laevulinic acid phenylhydrazone and 4-chloro-2-methylquinazoline, there was obtained 2-methyl-1-(2-methylquinazolin-4-yl)indol-3-ylacetic acid as an anhydrous syrup [NMR:, 2-$CH_3$(indole ring) at 7.6τ; 2-$CH_3$(quinazoline ring) at 8.1τ].

EXAMPLE 5

To a solution of 4-chloroquinazoline (16.4g.) in dry 1,2-dimethoxyethane (150ml.; dried over sodium aluminosilicate, molecular sieve type 4A; see Example 4) at ca. 50° C. was added a solution of laevulinic acid phenylhydrazone (20.6g.) in dry 1,2-dimethoxyethane (50ml., dried as above). The resulting clear solution was left overnight at 25° C. in a sealed vessel. The solvent was separated from the semi-solid precipitate which deposited by decantation, and the precipitate was triturated with dry 1,2-dimethoxyethane (50ml; dried as above). Filtration of the mixture gave laevulinic acid N'-(quinazolin4-yl)-N'-phenylhydrazone hydrochloride as a yellow-brown solid which was used without further purification.

The above hydrazone hydrochloride (27.0g.) was mixed with laevulinic acid (70g.) and heated at 95° – 98° C. for 16 hours. The reaction mixture was added to water (ca. 1 l.) and the resulting mixture was stirred at 25° C. for 3 hours. Filtration gave a yellow solid which was crystallised from methanol to give 2-methyl-1-(quinazolin-4yl)indol-3-ylacetic acid as a yellow solid, m.p. 234°–236° C.

In a similar manner, starting with the appropriate starting materials, the following compounds were obtained:

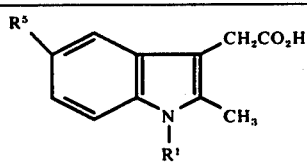

| $R^1$ | $R^5$ | m.p. (° C.) |
|---|---|---|
| 7-chloroquinazolin-4-yl | H | 202–205 |
| 2-methylquinazolin-4-yl | $CH_3O$** | 190–192* |
| 2-methylthioquinazolin-4-yl | $CH_3O$** | 175–178 |
| 7-chloroquinazolin-4-yl | $CH_3O$** | 202–204 |
| 7-chloroquinazolin-4-yl | $CH_3$ | 115–118 |

*recrystallised from ethyl acetate
**heating period for ring closure step was 2–6 hours.

EXAMPLE 6

The first stage described in Example 5 was repeated except that the starting materials were 4-chloro-2-methylquinazoline and laevulinic acid p-methoxyphenylhydrazone. A mixture of the laevulinic acid N'-(2-methylquinazolin-4-yl)-N'-p-methoxyphenylhydrazone hydrochloride so obtained (11.5g.) in N,N-dimethylformamide (100ml.; dried over molecular sieve Type 4A, see Example 4) was heated under reflux for 5 minutes. The mixture was rapidly cooled to 40°–50° C. and then evaporated in vacuo. Remaining traces of solvent were removed by azeotropic distillation with 1,1,2,2-tetrachloroethylene (3 × 50ml.). The residual yellow solid was stirred with water (250ml.) and the residue separated, dried in air, and recrystallised from ethyl acetate to give 5-methoxy-2-methyl-1-(2-methylquinazolin-4-yl)indol-3-ylacetic acid as a yellow crystalline solid, m.p. 190°–192° C. (after vacuum drying).

In a similar manner, starting with 4,7-dichloroquinazoline and laevulinic acid p-methoxyphenylhydrazone, there was obtained 1-(7-chloroquinazolin-4-yl)-5-methoxy-2-methylindol-3-ylacetic acid as a yellow solid, m.p. 203°–206° C. (after recrystallisation from methanol).

EXAMPLE 7

The first stage described in Example 5 was repeated except that the starting materials were 4,7-dichloroquinazoline and laevulinic acid p-methoxyphenylhydrazone.

Laevulinic acid (1600g.) was heated to 90°–95° C. and to it was added laevulinic acid N'-(7-chloroquinazolin-4-yl)-N'-p-methoxyphenylhydrazone hydrochloride (800g.) during 10 minutes, this hydrazone having been obtained as described immediately above. The dark solution was heated at 95°–110° C. for 4 hours, and then poured into a stirred mixture of water (1.8 l.) and chloroform (1.8 l.). The phases were separated and the aqueous phase extracted with chloroform (1.2 l.). The combined chloroform extracts were then shaken with a mixture of ammonia solution (d = 0.86, ca 1 l.) and water (8.0 l.). The phases were separated and the chloroform phase re-extracted with similar strength ammonia solution (2 l.). The combined aqueous phases were washed with n-butyl acetate (3 × 21.). The organic washings were discarded, and to the aqueous phase was added a filtered solution of calcium chloride (640g.) in water (3.2 l.) during 90 minutes, to give the calcium salt of 1-(7-chloroquinazolin-4-yl)-5-methoxy-2-methylindol-3-ylacetic acid, as a fine yellow precipitate. This was collected by filtration and stirred in water (8.0 l.) containing formic acid (0.8 l.) for 18 hours. The mixture was separated by filtration to give 1-(7-chloroquinazolin-4-yl)-5-methoxy-2-methylindol-3-ylacetic acid as the yellow hydrate, m.p. 110°–112° C. Crystalline material of m.p. 203°–205° C. was obtained by recrystallising the solid (dried at 40° C.) from ethyl acetate, methanol or toluene.

What we claim is:
1. A process for the preparation of a compound of the formula:

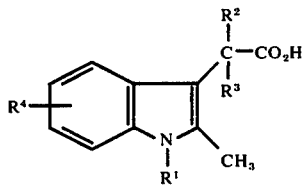

wherein $R^1$ stands for an unsubstituted quinazolin-4-yl radical or a quinazolin-4-yl radical bearing a $C_{1-5}$-alkyl, $C_{1-5}$-alkylthio or halogen substituent, and $R^2$ and $R^3$, which may be the same or different, stand for hydrogen or a methyl radical, and $R^4$ stands for hydrogen or a $C_{1-5}$-alkoxy or $C_{1-5}$-alkyl radical, and pharmaceutically-acceptable salts thereof, which comprises (a) reacting a compound of the formula:

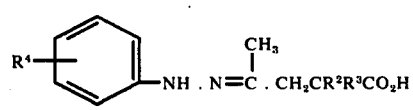

wherein $R^2$, $R^3$ and $R^4$ have the meanings stated above, with at least one molecular equivalent of a compound of the formula $R^1Y$, wherein $R^1$ has the meaning stated above and Y is a chlorine, bromine or iodine atom, in the presence of a solvent selected from the group consisting of 1,2-dimethoxyethane, diethyleneglycol dimethyl ether, dioxan, diphenyl ether, tetrahydrofuran and 1,2-dichloroethane, at 0° C to 50° C so as to give a compound of the formula:

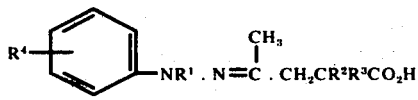

as its hydrochloride, hydrobromide or hydroiodide salt, respectively, and then (b) heating the hydrochloride, hydrobromide or hydroiodide salt of the compound of formula III in the presence of a compound selected from a Lewis acid; or sulfuric acid, perchloric acid, laevulinic acid, a polyphosphoric acid, formic acid or a $C_{1-5}$ alkyl ester thereof; or a hydrogen halide, at 40° C to 160° C, and when a pharmaceutically-acceptable salt is required, reacting the acid of formula I with a base affording a pharmaceutically-acceptable cation.

2. A process as claimed in claim 1 wherein the compound prepared is 1-(7-chloroquinazolin-4-yl)-5-methoxy-2-methylindol-3-ylacetic acid, 5-methoxy-2-methyl-1-(2-methylthioquinazolin-4-yl)indol-3-ylacetic acid, or a pharmaceutically-acceptable salt thereof.

3. A process as in claim 1 in which the stage (b) is carried out in a solvent selected from the group consisting of xylene and dimethylformamide.

* * * * *